(12) United States Patent
Epstein et al.

(10) Patent No.: US 7,803,141 B2
(45) Date of Patent: Sep. 28, 2010

(54) DEVICE AND METHOD FOR DIRECT DELIVERY OF A THERAPEUTIC USING NON-NEWTONIAN FLUIDS

(75) Inventors: Samuel J. Epstein, Watertown, MA (US); Wendy Naimark, Cambridge, MA (US); Toby Freyman, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 997 days.

(21) Appl. No.: 10/638,426

(22) Filed: Aug. 12, 2003

(65) Prior Publication Data

US 2005/0038406 A1    Feb. 17, 2005

(51) Int. Cl.
*A61M 5/00* (2006.01)

(52) U.S. Cl. .................. 604/264; 604/93.01

(58) Field of Classification Search .......... 604/44, 604/500, 506, 508, 522, 521, 73, 82, 83, 604/187, 181, 239, 246, 264, 272–275, 523, 604/537, 541, 543, 84, 92; 607/120, 119, 607/122; 433/89
See application file for complete search history.

(56) References Cited

U.S. PATENT DOCUMENTS

| | | | |
|---|---|---|---|
| 5,125,913 A * | 6/1992 | Quackenbush | 604/264 |
| 5,244,619 A * | 9/1993 | Burnham | 264/171.2 |
| 5,290,552 A * | 3/1994 | Sierra et al. | 424/94.64 |
| 5,662,619 A * | 9/1997 | Zarate | 604/272 |
| 6,132,396 A * | 10/2000 | Antanavich et al. | 604/82 |
| 6,132,405 A * | 10/2000 | Nilsson et al. | 604/264 |
| 6,132,436 A * | 10/2000 | Portney | 606/107 |
| 6,179,862 B1 * | 1/2001 | Sawhney | 606/214 |
| 6,409,972 B1 * | 6/2002 | Chan | 422/131 |
| 6,432,084 B1 * | 8/2002 | Levinson et al. | 604/118 |
| 6,485,462 B1 * | 11/2002 | Kriesel | 604/132 |
| 6,510,600 B2 * | 1/2003 | Yaron et al. | 29/428 |
| 6,878,143 B2 * | 4/2005 | Andersen | 604/270 |
| 6,921,381 B2 * | 7/2005 | Spero et al. | 604/82 |
| 7,066,914 B2 * | 6/2006 | Andersen | 604/270 |
| 2002/0026150 A1 | 2/2002 | Palasis et al. | |

(Continued)

FOREIGN PATENT DOCUMENTS

WO    WO 2004/014466 A    2/2004

OTHER PUBLICATIONS

"Bingham Fluid." Springer Online Reference Works. http:oem.springer.de/B/b110550.htm, access date Nov. 16, 2007.*

(Continued)

*Primary Examiner*—Nicholas D Lucchesi
*Assistant Examiner*—Christopher D Koharski
(74) *Attorney, Agent, or Firm*—Kenyon & Kenyon LLP

(57) ABSTRACT

A device, system, and method for direct delivery of a therapeutic to a target site that utilizes the non-Newtonian characteristics of shear thinning and shear thickening to allow easy passage of a therapeutic through a delivery lumen yet facilitate retention of the therapeutic in the target site. The device, system, and method includes increasing the shear rate or shear stress of a non-Newtonian fluid having therapeutic properties thereby increasing or decreasing the viscosity of the non-Newtonian fluid.

23 Claims, 4 Drawing Sheets

U.S. PATENT DOCUMENTS

2002/0077687 A1* 6/2002 Ahn .......................... 607/120
2002/0133139 A1 9/2002 Moulis
2003/0125665 A1 7/2003 Rosenman
2004/0030282 A1* 2/2004 Freyman et al. ............... 604/44
2004/0039351 A1* 2/2004 Barrett ...................... 604/272

OTHER PUBLICATIONS

"Blood Rheology: An Overview". http:www.mems.rice.edu/~dhruv/bloodrheo/, access date Nov. 16, 2007.*
Introduction to Biomedical Engineering. Enderle et al., pp. 187-189. Academic Press. Apr. 6, 2005.*

* cited by examiner

DEVICE AND METHOD FOR DIRECT DELIVERY OF A THERAPEUTIC USING NON-NEWTONIAN FLUIDS

FIELD OF INVENTION

The present invention relates to the direct delivery of a therapeutic to a target site. In particular, the present invention relates to a system, device and method for directly delivering a non-Newtonian fluid having therapeutic properties to a target site.

BACKGROUND

Therapeutics are often delivered directly to target areas of diseased tissue in various contemporary medical procedures. This direct delivery has proven to be an advantageous approach when treating numerous medical conditions. Advantages of this procedure are that only the target site may be exposed to the therapeutic and a controlled dose of therapeutic may be directly delivered to the target tissue.

Despite the advantages of direct delivery, one pronounced disadvantage is that the low viscosity of the therapeutic may result in the therapeutic being ejected or squeezed back through its point of entry in the target tissue. This problem is exacerbated in situations where the therapeutic is injected into an actively contracting tissue such as the myocardium of the heart. In such a case, the low-viscosity therapeutic may be ejected or squeezed out through its point of entry by the repeated expansion and contraction of the heart muscle. This unintended and unwanted leakage can result in an unascertainable dosage of the therapeutic being ultimately received by the target site, systemic distribution of the therapeutic, and arbitrary and unwanted interaction between leaked therapeutic and neighboring tissue and muscle.

As such, it is advantageous for a therapeutic to have a high solid content to retard its ejection from a target site. A therapeutic with a high solid to fluid ratio, however, may resist passage through a delivery lumen thereby necessitating the use of a solvent to provide an operative balance of solids to fluids. In these cases, however, the solvent employed may be toxic in relation to the target site or incompatible with the therapeutic.

There is, therefore, a need in the art for a method and apparatus that provides efficient direct delivery of a therapeutic to a target site while allowing for easy passage through a delivery lumen of a delivery device.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

SUMMARY OF INVENTION

Figure 1:
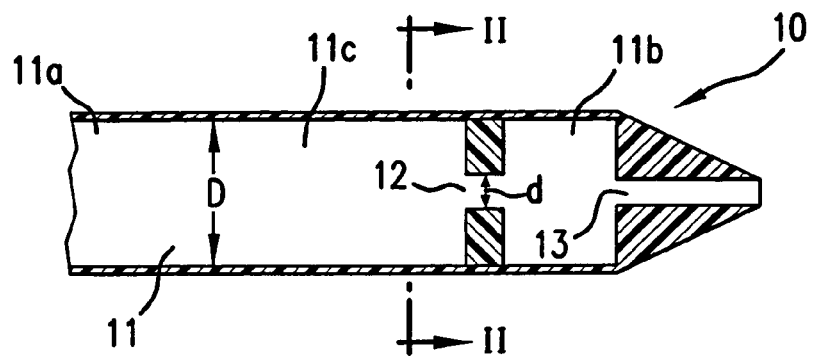
FIG. 1 is a side cross-sectional view of an embodiment of a device according to the present invention.

The present invention relates to a system, device and method for direct delivery of a therapeutic to a target site. To ensure retention of the therapeutic in the target site yet allow easy passage of the therapeutic through the delivery device, a non-Newtonian fluid bearing therapeutic properties is loaded into a delivery device. A non-Newtonian fluid displays non-Newtonian characteristics such as, for example, shear thinning and shear thickening and examples of non-Newtonian fluids include shear thinning fluids, shear thickening fluids, and Bingham fluids. As is generally known in the art, the viscosity of a shear thinning fluid decreases as the shear stress or shear rate in the shear thinning fluid increases and the viscosity of a shear thickening fluid increases as the shear stress or shear rate in the shear thickening fluid increases. A Bingham fluid behaves as a solid until the yield value is reached, at which point the fluid starts to flow. As the shear rate or shear stress continues to increase, the Bingham fluid may then exhibit Newtonian properties, such as shear-thinning or shear thickening properties.

With respect to an exemplary application of the present invention highlighting the general workings and principles of the invention, in one aspect the non-Newtonian fluid is a shear thinning fluid that is loaded into a delivery device according to the present invention. The shear thinning fluid may either act as a therapeutic itself or may be pre-loaded with a therapeutic prior to disposition in the delivery device. After the shear thinning fluid is loaded in the delivery device, the fluid is exposed to a viscosity adjuster. A viscosity adjuster includes any structure or any physical, chemical, or electrical mechanism or combination thereof that increases or decreases the shear stress or shear rate of the fluid to decrease or increase the viscosity of the fluid. In the case of a shear thinning fluid, the viscosity adjuster increases the shear stress or shear rate of the fluid, resulting in a decrease in the viscosity of the fluid as the fluid passes through the delivery device. This decrease in viscosity of the shear thinning fluid allows easy passage of the fluid through the delivery device. The fluid may then be injected into a target site where, in the reduction of shear, the fluid returns to its pre-shear viscosity level, which may facilitate retention of the therapeutic in the target site.

In another aspect of the present invention, the non-Newtonian fluid is a shear-thickening fluid that is loaded into a delivery device according to the present invention. The shear thickening fluid may also either act as a therapeutic itself or may be pre-loaded with a therapeutic prior to disposition in the delivery device. The fluid to solid content of a shear thickening fluid permits easy passage of the fluid through the delivery device. Prior to exiting the delivery device and at an appropriate distance proximal to the site of injection in the target site, the fluid is exposed to a viscosity adjuster that increases the shear stress or shear rate in the fluid resulting in an increase in the viscosity of the fluid. The fluid is then injected into a target site, where, because of the increased viscosity of the fluid, retention of the therapeutic is enhanced.

Therefore, the present invention provides a device for direct delivery of a therapeutic to a target site. The device generally comprises a channel that has a proximal end and a distal end, contains a non-Newtonian fluid having therapeutic properties, and is configured to expose the fluid to a viscosity adjuster.

The present invention also provides a system for direct delivery of a therapeutic to a target site. This system generally comprises a catheter, a channel defining a reservoir, and a viscosity adjuster. The channel is located at the distal end of the catheter and the reservoir defined by the channel contains a non-Newtonian fluid having therapeutic properties. The viscosity adjuster is adjustably positioned within the channel and is contactable with the reservoir.

The present invention also provides a method for directly delivering a non-Newtonian fluid having therapeutic properties to a target site. The method comprises loading the fluid in a channel that has a viscosity adjuster, adjusting the viscosity of the fluid by exposing the fluid to the viscosity adjuster of the channel, and delivering the fluid to a target site.

DETAILED DESCRIPTION OF THE INVENTION

Figure 2A:
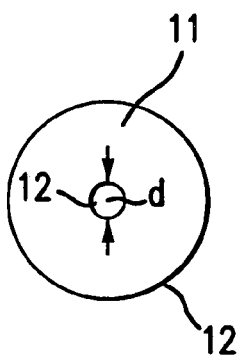
FIG. 2 is a cross-sectional view of the device of FIG. 1 and FIG. 7 along lines II-II.
Figure 2B:
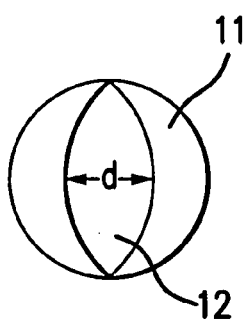
Figure 2C:
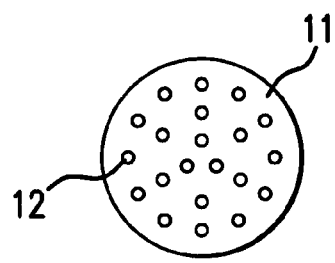

Referring to FIG. 1, device 10 according to the present invention generally comprises a channel 11 that has a proximal end 11a, a distal end 11b having an opening 13, and a lumen 11c extending therethrough. In the embodiment of device 10 shown in FIG. 1, the viscosity adjuster is a constricted flow orifice 12 defined by channel 11. Constricted flow orifice 12 is characterized by having a diameter d smaller than the maximum diameter D of channel 11 and acting to increase the shear rate of the non-Newtonian fluid as it passes therethrough. FIG. 2a, which is a cross-sectional view along lines II-II of FIG. 1, illustrates an exemplary design of flow orifice 12 that is defined by channel 11. Other exemplary designs of flow orifice 12 defined by channel 11 are illustrated in FIGS. 2b and 2c. As illustrated in FIG. 2a, channel 11 defines a single flow orifice 12 that has a diameter d that is smaller than the maximum diameter D of channel 11. As illustrated in FIG. 2b, channel 11 may define a flow orifice 12 that is oval-shaped and has a diameter d that is smaller than the maximum diameter D of channel 11. As seen in FIG. 2c, channel 11 may define a plurality of flow orifices 12 that each have a diameter smaller than the maximum diameter D of channel 11. The exact diameter d of flow orifice 12 is relative to, for example, the exact fluid being injected and the amount of force necessary to significantly change the viscosity of the fluid. The designs of flow orifices 12 illustrated in FIG. 2 are only exemplary and the present invention contemplates any design of channel 11 that defines a constricted flow orifice 12 that acts to increase the shear rate of a non-Newtonian fluid having therapeutic properties passing therethrough.

In embodiments where the non-Newtonian fluid is a shear-thickening fluid, flow orifice 12 is positioned near distal end 11b of channel 11 as illustrated in FIG. 1. Such a configuration allows easy passage of the shear thickening fluid along most of channel lumen 11c, yet leads to an increase in the shear rate of the fluid and thereby an increase in viscosity of the shear thickening fluid just prior to injection from opening 13 into the target site. Flow orifice 12 is positioned at an appropriate distance proximal to the injection site of the target site such that the change in viscosity that results from the increase in shear rate is significant enough to increase retention of the therapeutic in the target site. For example, the distance between flow orifice 12 and the injection site should be sufficiently long for any shearing to occur prior to contact with the target site yet short enough to not allow any relaxation of the fluid shearing properties prior to contact with the target tissue. Preferably, prior to exposure to the constricted flow orifice 12, the critical flow rate of the fluid is not exceeded, as a high flow rate through constricted flow orifice 12 may result in turbulent flow that may be significant enough to prematurely induce shear thickening.

In embodiments where the non-Newtonian fluid is a shear thinning fluid, channel 11 defines a series of constricted flow orifices 12 positioned along the entire length of channel 11. This configuration facilitates an increase in shear rate of the fluid as the fluid passes through channel lumen 11c from the proximal end 11a to the distal end 11b of channel 11 and thereby a decrease in the viscosity of the shear thinning fluid as the fluid passes through channel lumen 11c from the proximal end 11a to the distal end 11b of channel 11.

Figure 3:
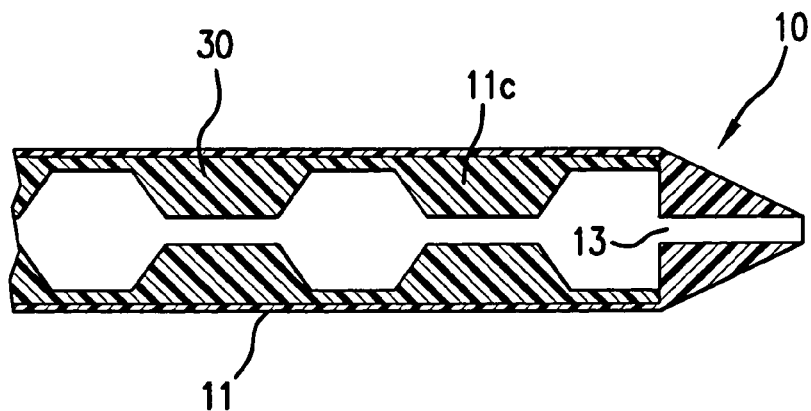
FIG. 3 is a side cross-sectional view of an embodiment of a device according to the present invention.
Figure 4:
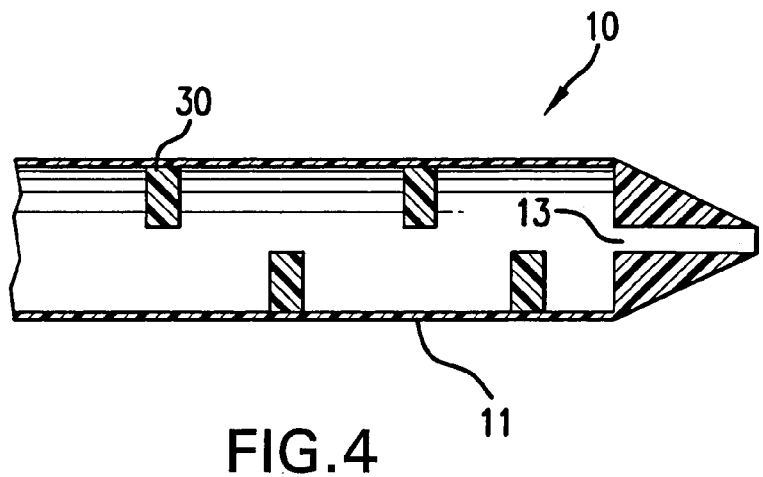
FIG. 4 is a side cross-sectional view of an embodiment of a device according to the present invention.
Figure 5:
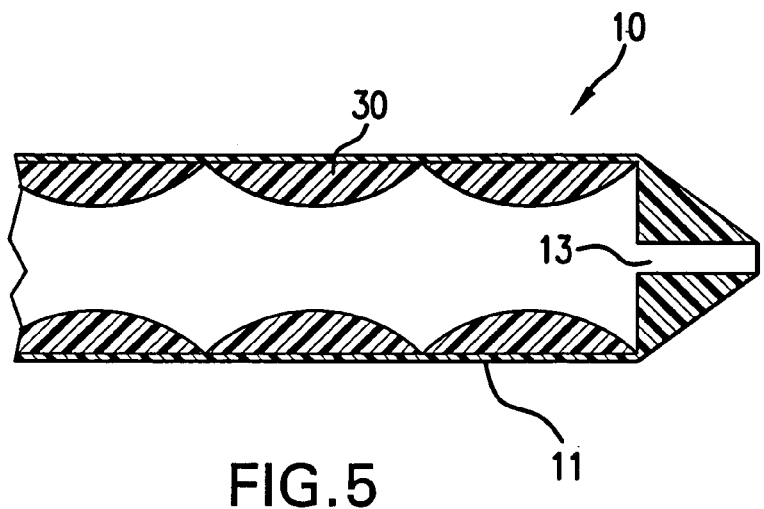
FIG. 5 is a side cross-sectional view of an embodiment of a device according to the present invention.

Referring to FIG. 3, in another embodiment of device 10, a viscosity adjuster comprises at least one protrusion 30 within or defined by channel 11 and preferably at least two protrusions 30 within or defined by channel 11. In the embodiment illustrated in FIG. 3, protrusions are in the form of truncated cones. The present invention, however, contemplates any form of protrusions 30 that act to collectively increase the shear rate of the fluid as the fluid is exposed thereto, including, for example, posts 30 as seen in FIG. 4 and ridges 30 as seen in FIG. 5. In embodiments where a shear-thinning fluid is utilized, protrusions 30 preferably extend along the entire length of channel 11, as seen in FIGS. 3-5, and in embodiments where a shear-thickening fluid is utilized, protrusions 30 are preferably located only at distal end 11b of channel 11, both for reasons discussed above.

As will be appreciated by one of skill in the art, by modifying the geometry and placement of protrusions 30, various degrees of shearing can be achieved and therefore the present invention also contemplates any such modifications being within the scope of the invention. Protrusions 30 and the portions of channel 11 defining constricted flow orifices 12 may be fabricated of any biocompatible material including stainless steel, nitinol, teflon, or any other biocompatible material currently used for direct injection catheters.

Figure 6:
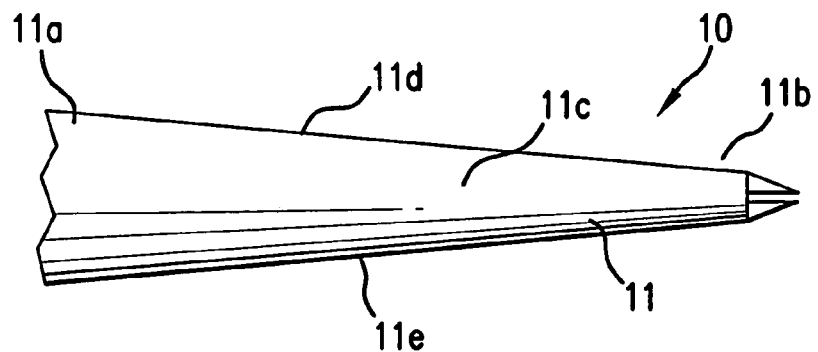
FIG. 6 is a side view of an embodiment of a device according to the present invention.

Referring to FIG. 6, in an alternative embodiment of device 10, the viscosity adjuster comprises an at least one surface of channel 11 that is tapered from proximal end 11a of channel 11 to distal end 11b of channel 11. Although in the embodiment of device 10 shown in FIG. 6, both surface 11d and surface 11e of channel 11 are tapered, the present invention also contemplates only one of surface 11d and 11e being tapered (not shown). This embodiment is particularly useful when using a shear thinning fluid, as the shear rate of the shear thinning fluid would increase as the fluid travels along the length of the channel 11 thereby decreasing the viscosity of the fluid and allowing easy passage of the fluid through channel lumen 11c.

Figure 7:
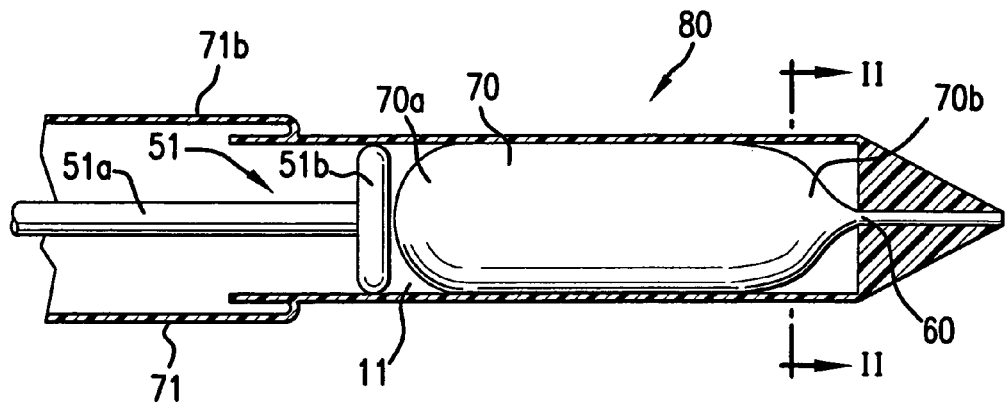
FIG. 7 is a side cross-sectional view of an embodiment of a system according to the present invention.

Referring to FIG. 7, the present invention also provides a system 80 for direct delivery of a therapeutic into a target site comprising a catheter 71, a channel 11 defining a reservoir 70, and a viscosity adjuster 51. The catheter 71 has a proximal end (not shown) and a distal end 71b and channel 11 is located at the distal end 71b of catheter 71. Reservoir 70 of channel 11 contains a non-Newtonian fluid having therapeutic properties and has a proximal end 70a, and a distal end 70b having an opening 60. The viscosity adjuster 51 also has a proximal end 51a and a distal end 51b, is adjustably positioned within channel 11, and is contactable with reservoir 70. In use, force is applied to viscosity adjuster 51 which, in turn, applies force to reservoir 70. The applied force to reservoir 70 increases the shear stress in the non-Newtonian fluid contained therein thereby increasing or decreasing the viscosity of the non-Newtonian fluid, depending on whether the non-Newtonian fluid is a shear-thinning or shear-thickening fluid.

Figure 8:
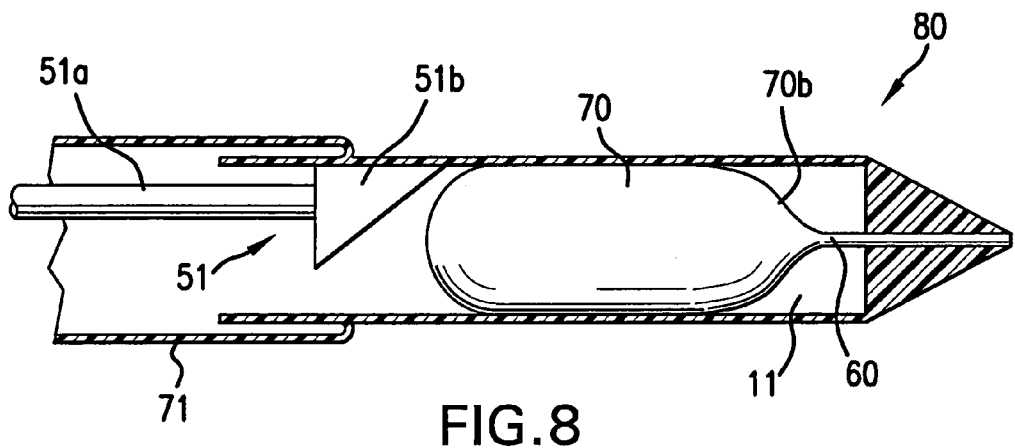
FIG. 8 is a side cross-sectional view of an embodiment of a system according to the present invention.
Figure 9:
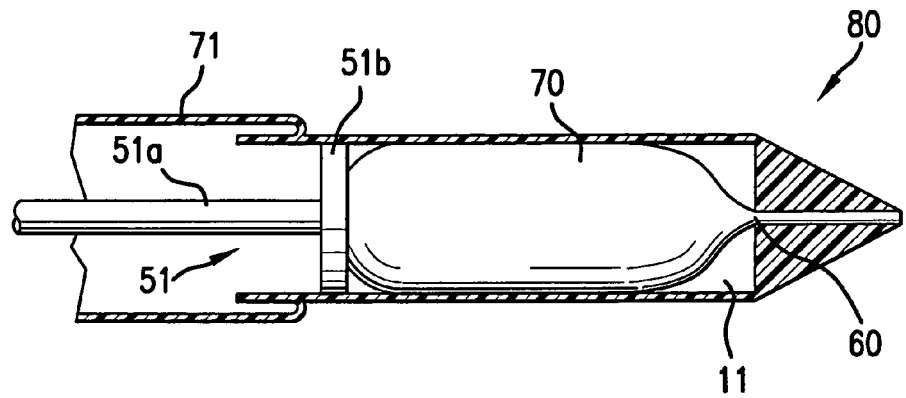
FIG. 9 is a side cross-sectional view of an embodiment of a system according to the present invention.

In the embodiment shown in FIG. 7, the viscosity adjuster is a plunger 51 and distal end 51b has a substantially planar surface. In an alternative embodiment of plunger 51, as seen in FIG. 8, distal end 51b is wedge-shaped to allow for contact with a greater surface area of reservoir 70. In yet another alternative embodiment of plunger 51, as seen in FIG. 9, plunger 51 is rotatable and distal end 51b is attached to reservoir 70. In this embodiment, in order to apply force to reservoir 70 and increase the shear stress in the non-Newtonian fluid therein, proximal end 51a of plunger 51 is rotated, which results in reservoir 70 being twisted thereby applying force to the non-Newtonian fluid therein.

Figure 10:
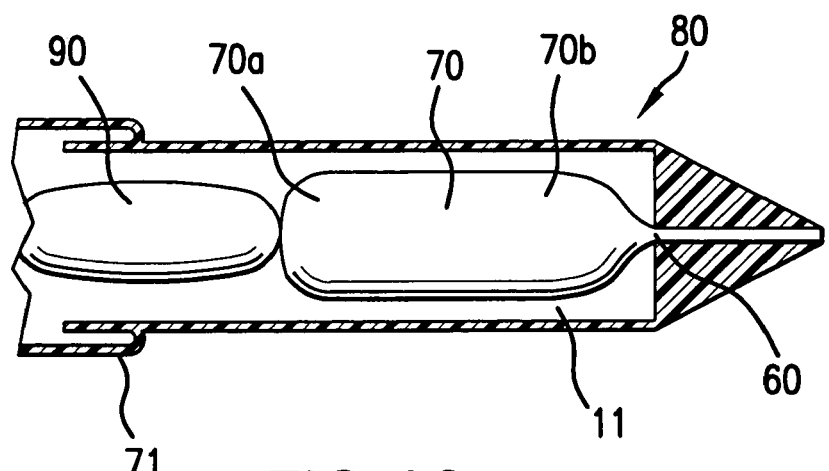
FIG. 10 is a side cross-sectional view of an embodiment of a system according to the present invention.

Referring to FIG. 10, in another embodiment, the viscosity adjuster of system 80 is not a plunger but an expandable balloon 90. In order to apply force to reservoir 70, balloon 90 is expanded and contacted with reservoir 70. Although FIG. 9 depicts balloon 90 adjacent the proximal end of reservoir 70, balloon 90 could be adjacent any surface of reservoir 70 as long as balloon 90 is in a position to apply force to reservoir 70.

Although in the aforementioned embodiments, the viscosity adjuster is in the form of a plunger or balloon, the present invention contemplates any other form of the viscosity adjuster that can apply force to reservoir 70 and thereby increase the shear stress in the non-Newtonian fluid contained therein resulting in an increase or decrease the viscosity of the non-Newtonian fluid (depending on whether the non-Newtonian fluid is a shear-thinning or shear-thickening fluid).

The aforementioned embodiments (illustrated in FIGS. 6-10) are particularly preferable when a shear-thinning fluid is utilized as the non-Newtonian fluid. Under preferred conditions, as the viscosity adjuster (51 or 90) moves along the longitudinal axis of channel 11 from proximal end 11a of channel 11 to distal end 11b of channel 11 urging the fluid out opening 60 of reservoir 70, the shear stress in the fluid increases. Because the viscosity of shear thinning fluids decrease as the shear stress in the fluids increases, under preferred conditions, the ease in which the shear-thinning fluid passes through channel 11 increases along the longitudinal axis of channel 11.

Figure 11:
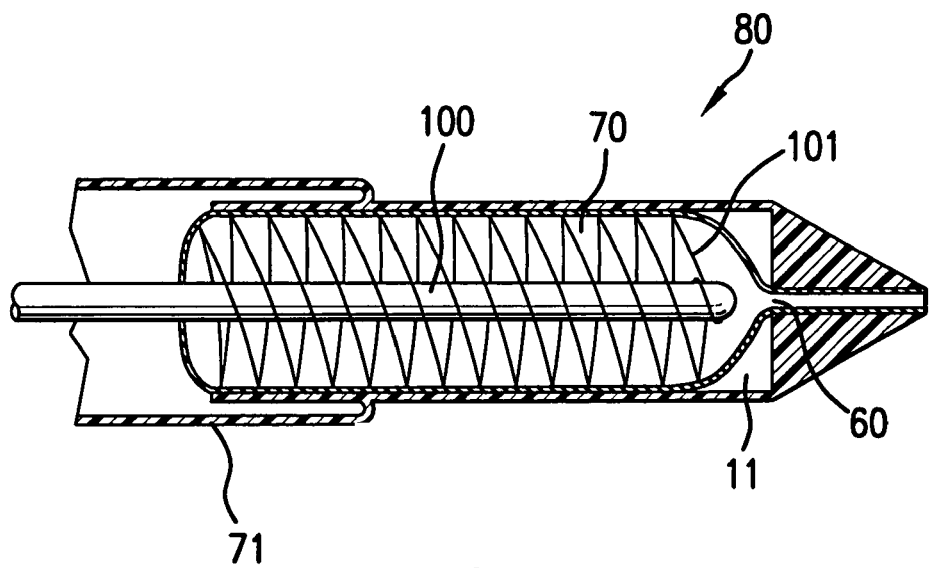
FIG. 11 is a side cross-sectional view of an embodiment of a system according to the present invention.

Referring to FIG. 11, the present invention also contemplates an alternative embodiment of a system 80 for direct delivery of a therapeutic to a target site comprising a catheter 71; a channel 11 defining a reservoir 70 that contains a non-Newtonian fluid having therapeutic properties; and a viscosity adjuster adjustably positioned within channel 11, and contactable with reservoir 70. In this embodiment, the viscosity adjuster is a screw extruder 100 with threading 101 that contacts channel 11. Screw extruder 100 can be rotated to effectively stir the non-Newtonian fluid and agitate the molecules contained therein (causing a reduction in molecular entanglements in the case of a shear thinning fluid) to increase the shear rate of the non-Newtonian fluid as well as extrude the fluid through opening 60. Preferably, screw extruder 100 extends along the entire length of reservoir 70 to increase the access of screw extruder 100 to the molecules of the fluid. Depending on whether the non-Newtonian fluid is a shear thinning or shear thickening fluid, increasing the shear rate will increase or decreases the viscosity of the non-Newtonian fluid. Although FIG. 7 depicts a viscosity adjuster that is a screw extruder 100 with threading 101 that contacts channel 11, the viscosity adjuster could be any structure that agitates the molecules of the non-Newtonian fluid contained in reservoir 70 to increase the shear rate thereof. For example, the viscosity adjuster could be a probe, such as an ultrasound or heat probe.

In order to further increase the shear stress or the shear rate of the non-Newtonian fluid according to the aforementioned embodiments of the present invention (utilizing a plunger 51, balloon 90 or screw extruder 100), opening 60 of reservoir 70 may be constricted as seen in FIG. 7. The present invention contemplates any design of opening 60 that is constricted that acts to increase the shear stress or the shear rate of the non-Newtonian fluid passing therethrough, such as, by way of example, the designs of flow orifice 12 depicted in FIG. 2. Another embodiment of opening 60 that is constricted is illustrated in FIG. 8, where distal end 70b of reservoir 70 defines an opening 60 that is tapered.

With respect to an exemplary use of a device according to the present invention, a non-Newtonian having therapeutic properties is loaded in channel 11 of a delivery device and urged through channel lumen 11c by any means known in the art. For example, a syringe, a mechanical pump or a squeezable bladder may be used to urge the fluid through channel lumen 11c. The viscosity of the non-Newtonian fluid is adjusted by exposing the fluid to a viscosity adjuster of channel 11. The viscosity adjuster may comprise, for example, a configuration of channel 11 that increases the shear rate of the non-Newtonian fluid, an element that is adjustably positioned within channel 11 to increase the shear stress of the non-Newtonian fluid, or an element that is adjustably positioned within channel 11 to increase the shear rate of the non-Newtonian fluid. Depending on whether the non-Newtonian fluid is a shear-thinning or shear thickening fluid, the increase in shear rate or shear stress either increases or decreases the viscosity of the non-Newtonian fluid. The non-Newtonian fluid then exits the opening 13/60 of channel 11 (or reservoir 70) and is then delivered to the target site. After leaving the delivery device, the therapeutic is better suited to remain within the target site, particularly when the target site is actively contracting.

The non-Newtonian fluid having therapeutic properties may either act as a therapeutic itself or be loaded with a therapeutic. Non-limiting examples of therapeutics include pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; dsRNA, naked DNA, cDNA, RNA; genomic DNA, cDNA or RNA in a non-infectious vector or in a viral vector and which further may have attached peptide targeting sequences; anti-sense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; enzymes such as heme oxygenase that produce anti-oxidants and have anti-inflammatory, vasodilatory, and anti-proliferative action; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin, hKIS, and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anticoagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, bone marrow derived extracellular matrix, in vivo bioengineered extracellular matrix, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK"), cladribine, and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), the family of tissue inhibitors of metalloproteinase ("TIMP"), and the family of bone morphogenic proteins ("BMPs"). The known proteins include BMP-2, BMP-3, BMP-4, BMP-5, BMP-6 (Vgr-1), BMP-7(OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

Non-limiting examples of shear thinning fluids include polymer solutions, large molecules, melts, and blends. Non-limiting examples of shear thickening fluids include lipids, ionic surfactants, nonionic surfactants, poly (vinyl chloride) pastes, semi-dilute starch solutions and starch solutions in alkaline solution media. Other non-Newtonian fluids according to the present invention include Bingham fluids such as slurries.

Organs and tissues that may be treated by the methods of the present invention include any mammalian tissue or organ, whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone.

The therapeutic agents can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

Having thus described the present invention with reference to certain of its preferred embodiments, it will now be further illustrated with the following example that may be followed in practicing the invention but which should not be construed as limiting the invention in any way.

EXAMPLE

In order to test the concept of shear-thinning as it relates to a model therapeutic, a highly concentrated DNA solution is formulated. At 20 mg/ml, aqueous DNA is essentially solid. The DNA solution of the present example is formulated to 100 mg/ml. This solution is loaded into a device according to the present invention and a 26-gauge needle is attached. The DNA solution passes through the needle tip despite the tremendous viscosity of the solution. The DNA solution that exits the tip of the needle appears to have the viscosity of water. After a few moments, the DNA solution returns to its original viscosity. Fluorescent analysis of the DNA solution that is loaded into the device according to the present invention and the DNA solution that exits the needle tip reveals that there is essentially no change in the concentration of the DNA.

The foregoing description and example have been set forth merely to illustrate the invention and are not intended to be limiting. Each of the disclosed aspects and embodiments of the present invention may be considered individually or in combination with other embodiments of the invention, other variations, and other aspects of the invention. Modifications of the disclosed embodiments incorporating the spirit and substance of the invention may occur to persons skilled in the art and such modifications are within the scope of the present invention. For example, although the viscosity adjustor of the device, system and method according to the present invention has been described in terms of a structural means of increasing the shear rate or shear stress of the non-Newtonian fluid having therapeutic properties, any other means of adjusting these parameters is contemplated by the present invention. For example, the viscosity adjuster of the present invention may be chemical, electrical, or other physical means (such as temperature) to increase the shear rate or shear stress of the fluid thereby increasing or decreasing the viscosity of the fluid.

We claim:

1. A device for direct delivery of a shear thickening fluid having therapeutic properties to a target site, the device comprising:
   a channel having a proximal end, a distal end and a central lumen extending therethrough, the central lumen having a longitudinal axis, the channel containing a shear thickening fluid having therapeutic properties, the channel configured to expose the shear thickening fluid to a viscosity adjuster;
   wherein the viscosity adjuster comprises at least two non-overlapping projections extending from one or more walls of the channel and leaving an open flow channel coincident with the central lumen's longitudinal axis,
   wherein the viscosity adjuster's at least two non-overlapping projections are located at the same point along the central lumen's longitudinal axis and define at least one constricted flow orifice perpendicular to the central lumen's longitudinal axis.

2. The device of claim 1, wherein the viscosity adjuster is at the distal end only of the lumen.

3. The device of claim 1, wherein the shear thickening fluid having therapeutic properties comprises a shear thickening fluid pre-loaded with a therapeutic.

4. The device of claim 3, wherein the therapeutic is a pharmaceutically active compound.

5. The device of claim 1, wherein at least one of the at least two non-overlapping projections comprises a post- or peg-like shape.

6. The device of claim 1, wherein at least one of the at least two non-overlapping projections comprises a truncated cone shape.

7. The device of claim 1, wherein at least one of the at least two non-overlapping projections comprises a ridged shape.

8. The device of claim 1, wherein the at least one constricted flow orifice comprises a single flow orifice having a circular shape.

9. The device of claim 1, wherein the at least one constricted flow orifice comprises a single flow orifice having an ovular shape.

10. The device of claim 1 wherein the at least one constricted flow orifice comprises a plurality of circular-shaped flow orifices.

11. The device of claim 1, wherein the at least two non-overlapping projections extend in a substantially perpendicular direction from the one or more walls of the channel.

12. The device of claim 1, wherein the open flow channel extends from the proximal end to the distal end of the channel.

13. The device of claim 1, wherein the open flow channel is continuous and straight.

14. The device of claim 1, wherein the projections comprise stainless steel, nitinol or Teflon™.

15. The device of claim 1, wherein the walls of the channel have no lateral openings.

16. The device of claim 1, wherein the projections are directly opposed to each other.

17. A method for directly delivering a shear thickening fluid having therapeutic properties to a target site, the method comprising:
    loading the fluid in a channel, the channel having a central lumen and a viscosity adjuster, the central lumen having a longitudinal axis, and the viscosity adjuster comprising at least two non-overlapping projections extending from one or more walls of the channel and leaving an open flow channel coincident with the central lumen's longitudinal axis;
    adjusting the viscosity of the fluid by exposing the fluid to the viscosity adjuster of the channel; and
    delivering the fluid to a target site,
    wherein the viscosity adjuster's at least two non-overlapping projections are located at the same point along the central lumen's longitudinal axis and define at least one constricted flow orifice perpendicular to the central lumen's longitudinal axis.

18. The method of claim 17, wherein adjusting the viscosity increases the viscosity of the shear thickening fluid.

19. The method of claim 17, wherein the viscosity adjuster is at the distal end only of the lumen.

20. The method of claim 17, wherein the shear thickening fluid having therapeutic properties comprises a shear thickening fluid pre-loaded with a therapeutic.

21. The method of claim 20, wherein the therapeutic is a pharmaceutically active compound.

22. The method of claim 17, wherein the walls of the channel have no lateral openings.

23. The method of claim 17, wherein the projections are directly opposed to each other.

* * * * *